United States Patent
Lai

(10) Patent No.: US 7,258,547 B1
(45) Date of Patent: Aug. 21, 2007

(54) PRESS-TYPE BIT-HOLDING MECHANISM OF A DENTAL HIGH-SPEED HANDSET

(75) Inventor: Aling Lai, Taichung (TW)

(73) Assignee: Thunder Tiger Corporation, Taichung (TW)

( * ) Notice: Subject to any disclaimer, the term of this patent is extended or adjusted under 35 U.S.C. 154(b) by 0 days.

(21) Appl. No.: 11/451,393

(22) Filed: Jun. 13, 2006

(51) Int. Cl.
*A61C 1/14* (2006.01)

(52) U.S. Cl. .................................. 433/129; 433/127

(58) Field of Classification Search ............... 433/127, 433/128, 129; 279/43, 43.4, 43.2
See application file for complete search history.

(56) References Cited

U.S. PATENT DOCUMENTS

| | | | | |
|---|---|---|---|---|
| 4,874,314 A | * | 10/1989 | Fleer et al. .................. | 433/129 |
| 5,040,980 A | * | 8/1991 | Heil ............................ | 433/127 |
| 5,074,789 A | * | 12/1991 | Shibata ....................... | 433/129 |
| 5,165,896 A | * | 11/1992 | Hain et al. .................. | 433/129 |
| 5,688,122 A | * | 11/1997 | Teufelberger et al. ...... | 433/127 |
| 5,730,596 A | * | 3/1998 | Rosenstatter ................ | 433/127 |
| 6,190,168 B1 | * | 2/2001 | Bowen ........................ | 433/127 |
| 6,227,854 B1 | * | 5/2001 | Helfenbein et al. ......... | 433/128 |
| 2005/0142516 A1 | * | 6/2005 | Cohen ......................... | 433/134 |
| 2006/0281048 A1 | * | 12/2006 | Bailey et al. ............... | 433/127 |
| 2006/0286504 A1 | * | 12/2006 | Maitre et al. ............... | 433/129 |

\* cited by examiner

*Primary Examiner*—Ralph A. Lewis
(74) *Attorney, Agent, or Firm*—Rosenberg, Klein & Lee

(57) ABSTRACT

A press-type bit-holding mechanism of a dental high-speed handset, including a hollow rotary shaft, a push button accommodated in the hollow rotary shaft and a holder barrel also accommodated in the hollow rotary shaft. The push button has a first coupling section formed with two opposite splits and two opposite first projecting posts. The first projecting posts and the splits are interlaced with each other. The holder barrel has a second coupling section has two second splits and two second projecting posts complementary to the first splits and the first projecting posts of the first coupling section of the first coupling section of the push button.

2 Claims, 5 Drawing Sheets

PRESS-TYPE BIT-HOLDING MECHANISM OF A DENTAL HIGH-SPEED HANDSET

BACKGROUND OF THE INVENTION

The present invention is related to a press-type bit-holding mechanism of a dental high-speed handset, in which the holder barrel and the push button can be more firmly located to more truly transmit the power. In addition, by means of pressing the push button, the bit can be conveniently extracted and replaced.

In general, the treatment of a dentist to a patient includes prosthesis of caries, grinding, etc. Various bits can be installed on a dental handset, such as an engine bur and a grinding head. Therefore, the handset is most frequently used instrument among all the dental implements. In curing work, the bit is placed in a patient's oral cavity and driven. Therefore, it is necessary to precisely and firmly locate the bit. In case the bit loosens when a dentist works, the dentist will put the patient's life in great danger.

In the conventional bit locating mechanism, a holder barrel is installed in a hollow rotary shaft. The thickness of the holder barrel is tapered from one end to the other end. The bit is held in the holder barrel. The holder barrel is tightly fitted in the hollow rotary shaft to fix the bit. A push button is fitted in the hollow rotary shaft and drivingly connected with the holder barrel via a linking section, whereby the holder barrel is rotatable along with the rotary shaft. By means of pressing the push button, the thicker end of the holder barrel can be retracted from the hollow rotary shaft to detach the bit from the rotary shaft.

According to the above arrangement, the holder barrel is simply drivingly connected with the push button via the linking section. The connecting strength is insufficient so that it is possible that the holder barrel unexpectedly drops out of the rotary shaft. As a result, the bit can be hardly firmly located. Therefore, due to vibration in operation, the bit and the holder barrel are easy to wear. In order to more firmly lock the bit with the holder barrel, it is necessary to enhance the precision of the dimension of the holder barrel and the bit and promote the quality of the material thereof. This inevitably will increase the cost.

SUMMARY OF THE INVENTION

It is therefore a primary object of the present invention to provide a press-type bit-holding mechanism of a dental high-speed handset, in which the holder barrel and the push button can be more firmly located to prolong the using life of the bit-holding mechanism.

According to the above object, the press-type bit-holding mechanism of the dental high-speed handset of the present invention includes:

a hollow rotary shaft formed with an axial receiving tunnel and having a first end section and a second end section opposite to the first end section, the first end being depressed to form an abutting section defining a hexagonal hole;

a push button having a substantially annular first coupling section and a fixing section integrally connected with the first coupling section, the first coupling section defining a first coupling hole, the first coupling section being formed with two opposite splits in a direction distal from the fixing section, the first coupling section further having two first projecting posts opposite to each other, the first projecting posts and the splits being interlaced with each other, the fixing section being adjoined with a stop shoulder section, the push button being accommodated in the receiving tunnel of the hollow rotary shaft with the shoulder section abutting against the abutting section of the first end section, the fixing section having a hexagonal shape adapted to the hexagonal hole of the abutting section, the fixing section extending through the hexagonal hole out from the first end section, whereby the push button and the hollow rotary shaft cannot be rotated relative to each other; and a holder barrel accommodated in the receiving tunnel of the hollow, rotary shaft, the holder barrel having a substantially annular second coupling section defining a second coupling hole, the second coupling section having two splits and two projecting posts complementary to the splits and the projecting posts of the first coupling section, the holder barrel having a frictional section adjacent to the second coupling section, the frictional section having a thickness larger than that of the second coupling section, the holder barrel further having a stop flange section distal from the second coupling section and adjacent to the frictional section, the flange section having a diameter larger than a diameter of the receiving tunnel of the hollow rotary shaft, the flange section abutting against the second end section of the hollow rotary shaft.

The present invention can be best understood through the following description and accompanying drawings wherein:

DETAILED DESCRIPTION OF THE PREFERRED EMBODIMENTS

Figure 1:
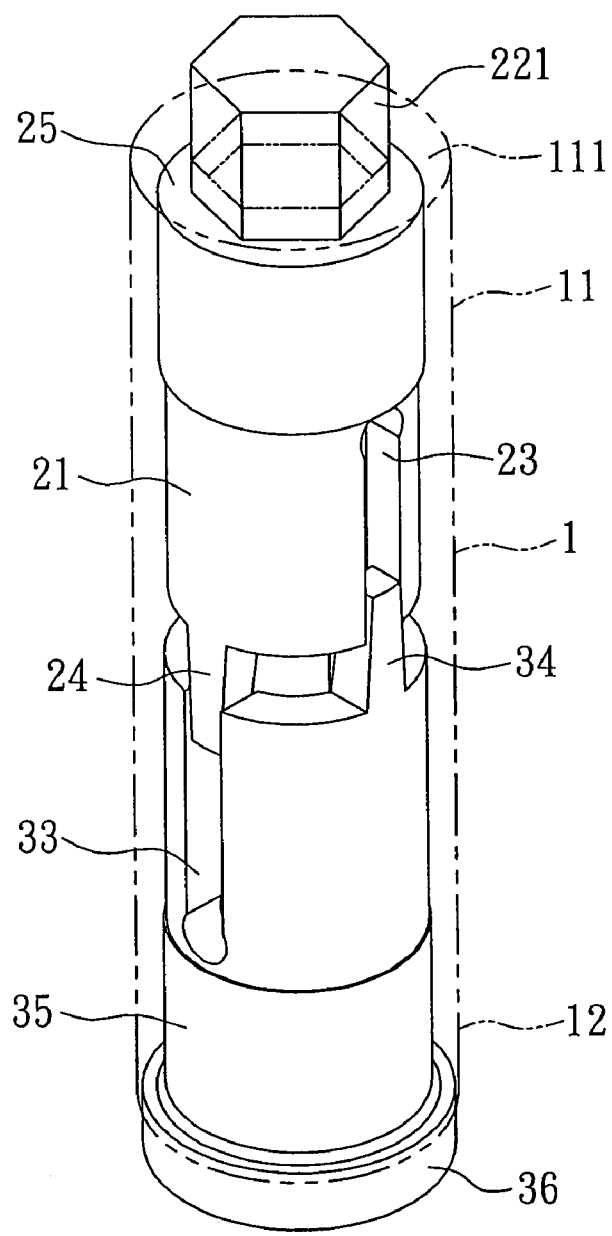
FIG. 1 is a perspective assembled view of the present invention, in which the rotary shaft is shown by phantom line.
Figure 2:
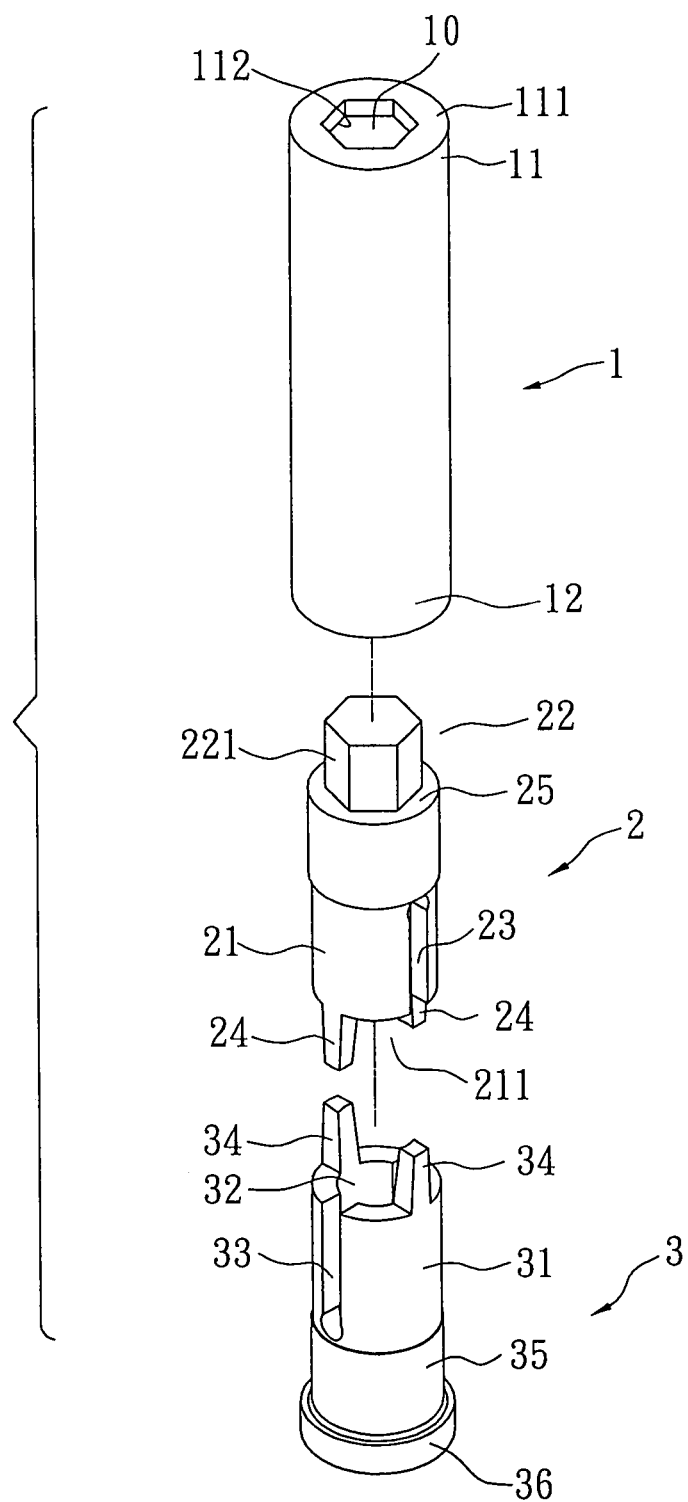
FIG. 2 is a perspective exploded view of the present invention.
Figure 3:
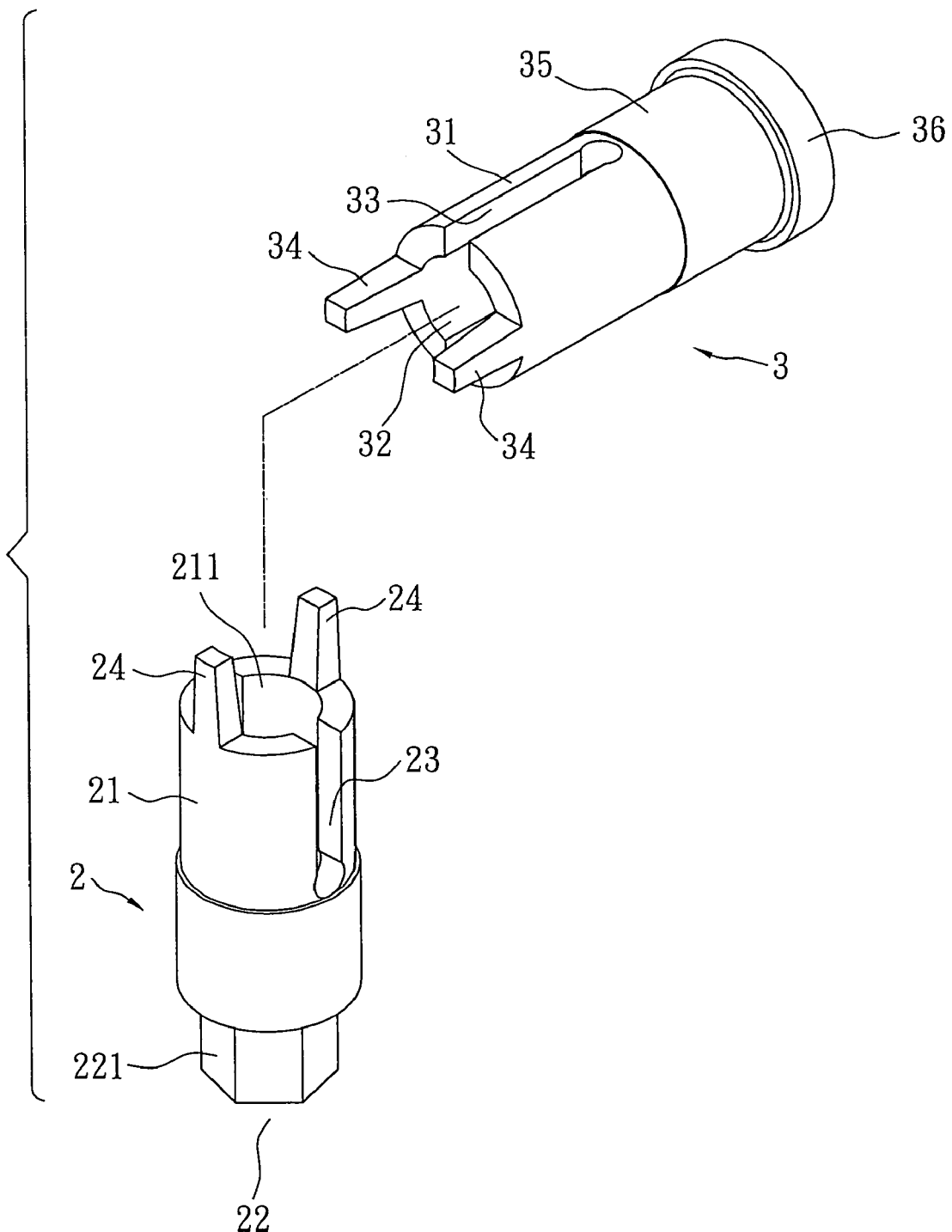
FIG. 3 is a perspective view showing the holder barrel and push button of the present invention.

Please refer to FIGS. 1 to 3. The press-type bit-holding mechanism of the dental high-speed handset of the present invention includes a hollow rotary shaft 1, a push but ton 2 and a holder barrel 3.

The hollow rotary shaft 1 is formed with an axial receiving tunnel 10 and has a first end section 11 and a second end section 12 opposite to the first end section 11. The first end 11 is depressed to form an abutting section 111 defining a hexagonal hole 112.

The push button 2 has a substantially annular first coupling section 21 and a fixing section 22 integrally connected with the first coupling section 21. The first coupling section 21 defines a first coupling hole 211.

The first coupling section 21 is formed with two opposite splits 23 in a direction distal from the fixing section 22. In addition, the first coupling section 21 has two first projecting posts 24 opposite to each other. The first projecting posts 24 and the splits 23 are interlaced with each other. The fixing section 22 is immediately adjoined with a stop shoulder section 25. The push button 2 is accommodated in the receiving tunnel 10 of the hollow rotary shaft 1 with the shoulder section 25 abutting against the abutting section 111 of the first end section 11.

The fixing section 22 has a hexagonal shape 221 adapted to the hexagonal hole 112 of the abutting section 111, whereby the fixing section 22 can extend through the hexagonal hole 112 out from the first end section 11. Accordingly, the push button 2 and the hollow rotary shaft 1 cannot be rotated relative to each other.

Figure 4:
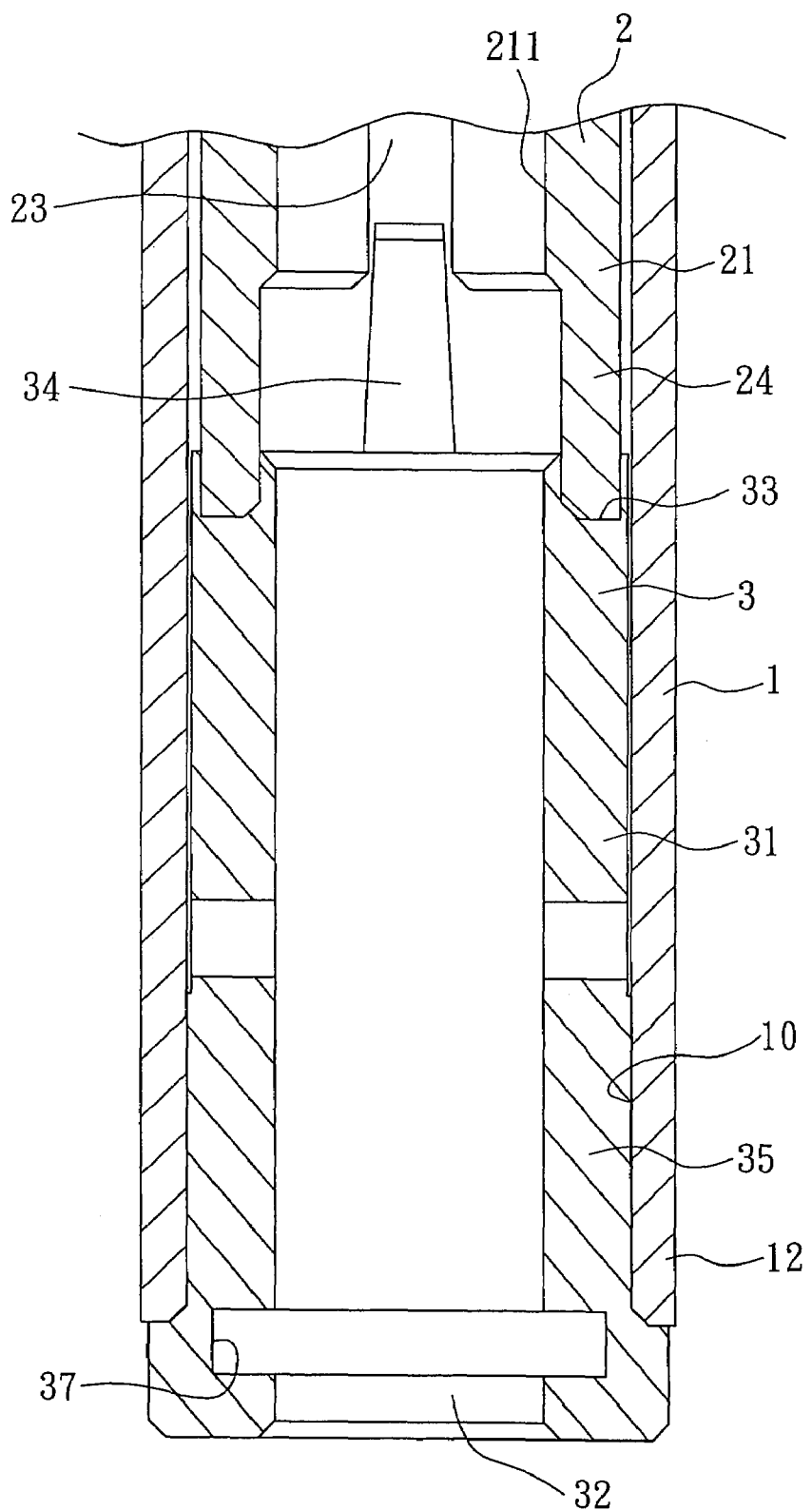
FIG. 4 is a sectional view of a part of the present invention.

The holder barrel 3 is also accommodated in the receiving tunnel 10 of the hollow rotary shaft 1. The holder barrel 3 has a substantially annular second coupling section 31 defining a second coupling hole 32. The second coupling section 31 has two splits 33 and two projecting posts 34 complementary to the splits 23 and the projecting posts 24 of the first coupling section 21. In addition, the holder barrel 3 has a frictional section 35 adjacent to the second coupling section 31. The frictional section 35 has a thickness larger than that of the second coupling section 31. The holder barrel 3 further has a stop flange section 36 distal from the second coupling section 31 and immediately adjacent to the frictional section 35. The flange section 36 has a diameter larger than the diameter of the receiving tunnel 10 of the hollow rotary shaft 1. In addition, the flange section 36 abuts against the second end section 12 of the hollow rotary shaft 1 as shown in FIG. 4. An inner circumference of the wall of the second coupling hole 32 is formed with an annular groove 37 between the flange section 36 and the frictional section 35 as shown in FIG. 4.

Figure 5:
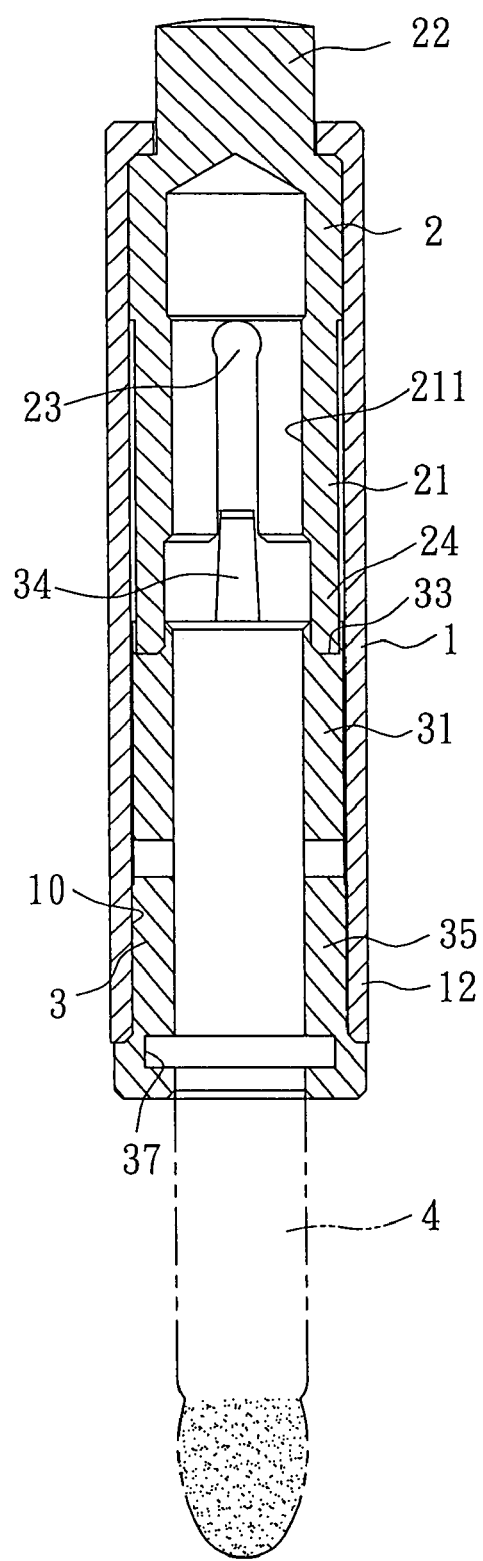
FIG. 5 is a sectional view of the present invention, showing that an engine bur is inserted into the hollow rotary shaft.

Referring to FIGS. 4 and 5, with an engine bur exemplified, the engine bur 4 is inserted into the second coupling hole 32 of the holder barrel 3 and extended to the first coupling hole 211 of the push button 2. The frictional section 35 of the holder barrel 3 is tightly fitted in the second end section 12 of the hollow rotary shaft 1. The second coupling section 31 of the holder barrel 3 is stretched open by the engine bur 4 to abut against the wall of the hollow rotary shaft 1. Similarly, the engine bur 4 also stretches open the first coupling section 21 of the push button 2 to abut against the hollow rotary shaft 4. Therefore, the engine bur 4, the hollow rotary shaft 2 and the push button 3 are tightly frictionally fitted and locked with each other. In addition, the projecting posts 24 of the push button 2 are inserted into the splits 33 of the holder barrel 3, while the projecting posts 34 of the holder barrel 3 are inserted into the splits 23 of the push button 2. Therefore, the holder barrel 3 and the push button 2 can be more firmly located to more truly transmit the power.

When it is desired to extract the engine bur 4, a dentist only needs to press the fixing section 22 of the push button 2. At this time, the projecting posts 24 of the push button 2 compress the holder barrel 3 and make the frictional section 35 of the holder barrel 3 get out of the receiving tunnel 10 of the hollow rotary shaft 1. Under such circumstance, the engine bur 4 is extracted out of the hollow rotary shaft 1. Such operation is quite convenient.

The above embodiments are only used to illustrate the present invention, not intended to limit the scope thereof.

Many modifications of the above embodiments can be made without departing from the spirit of the present invention.

What is claimed is:

1. A press-type bit-holding mechanism of a dental high-speed handset, comprising:
   a hollow rotary shaft formed with an axial receiving tunnel and having a first end section and a second end section opposite to the first end section, the first end being depressed to form an abutting section defining a hexagonal hole;
   a push button having a substantially annular first coupling section and a fixing section integrally connected with the first coupling section, the first coupling section defining a first coupling hole, the first coupling section being formed with two opposite splits in a direction distal from the fixing section, the first coupling section further having two first projecting posts opposite to each other, the first projecting posts and the splits being interlaced with each other, the fixing section being adjoined with a stop shoulder section, the push button being accommodated in the receiving tunnel of the hollow rotary shaft with the shoulder section abutting against the abutting section of the first end section, the fixing section having a hexagonal shape adapted to the hexagonal hole of the abutting section, the fixing section extending through the hexagonal hole out from the first end section, whereby the push button and the hollow rotary shaft cannot be rotated relative to each other; and
   a holder barrel accommodated in the receiving tunnel of the hollow rotary shaft, the holder barrel having a substantially annular second coupling section defining a second coupling hole, the second coupling section having two splits and two projecting posts complementary to the splits and the projecting posts of the first coupling section, the holder barrel having a frictional section adjacent to the second coupling section, the frictional section having a thickness larger than that of the second coupling section, the holder barrel further having a stop flange section distal from the second coupling section and adjacent to the frictional section, the flange section having a diameter larger than a diameter of the receiving tunnel of the hollow rotary shaft, the flange section abutting against the second end section of the hollow rotary shaft.

2. The press-type bit-holding mechanism of the dental high-speed handset as claimed in claim 1, wherein an inner circumference of a wall of the second coupling hole is formed with an annular groove between the flange section and the frictional section.

* * * * *